US012797011B2

(12) United States Patent
Zhong

(10) Patent No.: US 12,797,011 B2
(45) Date of Patent: Nov. 17, 2026

(54) SIGNAL PROCESSING METHOD AND APPARATUS, AND ELECTRONIC DEVICE

(71) Applicant: VIVO MOBILE COMMUNICATION CO., LTD., Dongguan (CN)

(72) Inventor: Lihao Zhong, Dongguan (CN)

(73) Assignee: VIVO MOBILE COMMUNICATION CO., LTD., Dongguan (CN)

( * ) Notice: Subject to any disclaimer, the term of this patent is extended or adjusted under 35 U.S.C. 154(b) by 465 days.

(21) Appl. No.: 18/534,550

(22) Filed: Dec. 8, 2023

(65) Prior Publication Data

US 2024/0099664 A1 Mar. 28, 2024

Related U.S. Application Data

(63) Continuation of application No. PCT/CN2022/097309, filed on Jun. 7, 2022.

(30) Foreign Application Priority Data

Jun. 10, 2021 (CN) ........................ 202110651546.3

(51) Int. Cl.
*A61B 5/00* (2006.01)
*A61B 5/024* (2006.01)

(52) U.S. Cl.
CPC .......... *A61B 5/721* (2013.01); *A61B 5/02416* (2013.01)

(58) Field of Classification Search
CPC ............................ A61B 5/721; A61B 5/02416
See application file for complete search history.

(56) References Cited

U.S. PATENT DOCUMENTS

2009/0005695 A1 1/2009 Kosuda et al.
2010/0145171 A1 6/2010 Park et al.
2012/0296221 A1 11/2012 Morren
2014/0221848 A1 8/2014 Nagasaka
(Continued)

FOREIGN PATENT DOCUMENTS

CN 104161505 A 11/2014
CN 105943015 A 9/2016
(Continued)

OTHER PUBLICATIONS

Extended European Search Report issued in related European Application No. 22819507.9, mailed Sep. 27, 2024, 10 pages.
(Continued)

*Primary Examiner* — Ricky Go
(74) *Attorney, Agent, or Firm* — IPX PLLC

(57) ABSTRACT

A signal processing method and apparatus, and an electronic device are provided. The method includes: obtaining a first pulse wave signal and motion signals in multi-dimensional directions, where the first pulse wave signal includes motion noise; performing independent filtering processing on the motion signal in each dimensional direction, and determining a noise estimated value corresponding to each dimensional direction; and using the noise estimated values in the multi-dimensional directions as parallel input parameters, using the first pulse wave signal as an input parameter, and performing filtering processing on the first pulse wave signal, to obtain a second pulse wave signal.

15 Claims, 3 Drawing Sheets

(56) References Cited

U.S. PATENT DOCUMENTS

| | | | | |
|---|---|---|---|---|
| 2015/0065896 | A1* | 3/2015 | Takahashi | A61B 5/7207 600/500 |
| 2017/0241799 | A1 | 8/2017 | Yanni | |
| 2017/0325750 | A1* | 11/2017 | Tanabe | A61B 5/7278 |
| 2017/0367657 | A1 | 12/2017 | Pande et al. | |
| 2019/0008458 | A1 | 1/2019 | van Dinther et al. | |
| 2020/0196880 | A1* | 6/2020 | Kwon | A61B 5/02416 |
| 2020/0305798 | A1 | 10/2020 | Ishikawa et al. | |
| 2020/0345252 | A1 | 11/2020 | Huijbregts et al. | |
| 2022/0096016 | A1* | 3/2022 | Tsujikawa | A61B 5/024 |

FOREIGN PATENT DOCUMENTS

| | | | |
|---|---|---|---|
| CN | 106691425 | A | 5/2017 |
| CN | 108478206 | A | 9/2018 |
| CN | 108652609 | A | 10/2018 |
| CN | 108937878 | A | 12/2018 |
| CN | 109222948 | A | 1/2019 |
| CN | 109512416 | A | 3/2019 |
| CN | 109512418 | A | 3/2019 |
| CN | 109864713 | A | 6/2019 |
| CN | 109965861 | A | 7/2019 |
| CN | 110151158 | A | 8/2019 |
| CN | 111084618 | A | 5/2020 |
| CN | 111643053 | A | 9/2020 |
| CN | 113349752 | A | 9/2021 |
| CN | 113397497 | A | 9/2021 |
| KR | 20100065084 | A | 6/2010 |

OTHER PUBLICATIONS

Chowdhury Sayeed Shafayet et al: "Real-Time Robust Heart Rate Estimation From Wrist—Type PPG Signals Using Multiple Reference Adaptive Noise Cancellation", IEEE Journal of Biomedical and Health Informatics, Mar. 2018.

First Office Action issued in related Chinese Application No. 202110651546.3, mailed Feb. 21, 2024, 9 pages.

Hao Zhang, "Research on blood oxygen saturation measurement system during exercise", Telecommunications Information, Sep. 10, 2017.

Yu Tang, "Applicaiton of adaptive filtering algorithm in extraction of heart rat using optoelectronic technology", Laser&Infrafed vol. 47 No. Jan. 1, 2017.

Dong E, "Design on ear photoplethysmography sensor with movement interference cancellation", Transducer and Microsystem Technologies, vol. 8, Aug. 20, 2012.

International Search Report issued in corresponding International Application No. PCT/CN2022/097309, mailed Sep. 13, 2022, 6 pages.

Guangming Fu et al, "Heart rate estimation based on cascaded LMS adaptive filtering PPG signal" Electronic Measuremeant Technology, ISSN:1002-7300, Nov. 23, 2019.

* cited by examiner

SIGNAL PROCESSING METHOD AND APPARATUS, AND ELECTRONIC DEVICE

CROSS-REFERENCE TO RELATED APPLICATIONS

This application is a continuation of International Application No. PCT/CN2022/097309, filed on Jun. 7, 2022, which claims priority to Chinese Patent Application No, 202110651546.3, filed Jun. 10, 2021, The entire contents of each of the above-identified applications are expressly incorporated herein by reference.

TECHNICAL FIELD

This application is directed to the field of signal processing technologies, and in particular, to a signal processing method and apparatus, and an electronic device.

BACKGROUND

When a user is in motion, a pulse wave signal acquired by a device includes motion noise. If a heart rate of the user is estimated based on the pulse wave signal, a problem of relatively low estimation accuracy is caused.

therefore, it is necessary to process the signal acquired by the device.

SUMMARY

A signal processing method and apparatus, and an electronic device, are provided.

According to a first aspect, an embodiment of this application provides a signal processing method, where the method includes: obtaining a first pulse wave signal and motion signals in multi-dimensional directions, where the first pulse wave signal includes motion noise; performing independent filtering processing on the motion signal in each dimensional direction, and determining a noise estimated value corresponding to each dimensional direction; and using the noise estimated values in the multi-dimensional directions as parallel input parameters, using the first pulse wave signal as an input parameter, and performing filtering processing on the first pulse wave signal, to obtain a second pulse wave signal.

According to a second aspect, an embodiment of this application provides a signal processing apparatus, where the apparatus includes: an obtaining module, configured to obtain a first pulse wave signal and motion signals in multi-dimensional directions, where the first pulse wave signal includes motion noise; a first processing module, configured to perform independent filtering processing on the motion signal in each dimensional direction, and determine a noise estimated value corresponding to each dimensional direction; and a second processing module, configured to use the noise estimated values in the multi-dimensional directions as parallel input parameters, use the first pulse wave signal as an input parameter, and perform filtering processing on the first pulse wave signal, to obtain a second pulse wave signal.

According to a third aspect, an embodiment of this application provides an electronic device, including a processor, a memoir, and a program or an instruction stored in the memory and runnable on the processor, where the program or the instruction is executed by the processor to implement the steps of the method according to the first aspect.

According to a fourth aspect, an embodiment of this application provides a readable storage medium, storing a program or an instruction, where the program or the instruction is executed by a processor to implement the steps of the method according to a first aspect.

According to a fifth aspect, an embodiment of this application provides a chip, including a processor and a communication interface, where the communication interface is coupled to the processor, and the processor is configured to run a program or instruction to implement the method according to the first aspect.

DETAILED DESCRIPTION

The embodiments of this application are described in the following with reference to the accompanying drawings in the embodiments of this application. Apparently, the described embodiments are some rather than all of the embodiments of this application. All other embodiments obtained by a person of ordinary skill in the art based on the embodiments of this application fall within the protection scope of this application.

The specification and claims of this application, and terms "first" and "second" are used to distinguish similar objects, but are not used to describe a specific sequence or order. It should be understood that the data termed in such a way are interchangeable in appropriate circumstances, so that the embodiments of this application can be implemented in orders other than the order illustrated or described herein. In addition, the objects distinguished by "first" and "second" are usually of a same type, without limiting a quantity of objects, for example, there may be one or more first objects. In addition, "and/or" in the description and the claims means at least one of the connected objects, and the character "/" in this specification generally indicates an "or" relationship between the associated objects.

A signal processing method provided in the embodiments of this application are described in detail below with reference to the accompanying drawings by using specific embodiments and application scenarios thereof.

Figure 1:
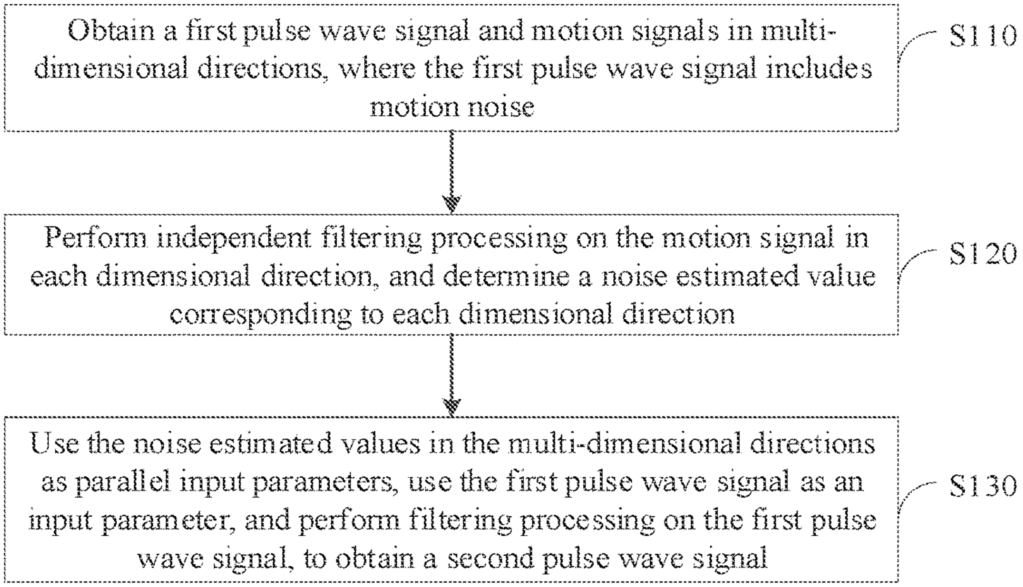
FIG. 1 is a flowchart of a signal processing method according to an embodiment of the present disclosure.

Referring to FIG. 1, a signal processing method provided in this embodiment may include the following step S110 to step S130.

Step S110: Obtain a first pulse wave signal and motion signals in multi-dimensional directions, where the first pulse wave signal includes motion noise.

In an embodiment of the present disclosure, the first pulse wave signal may be a pulse wave signal acquired by an electronic device, and the motion signals may be motion signals that are of the electronic device and that correspond to the multi-dimensional directions. The electronic device may be a smart wearable device such as a smartwatch or a smart band. A user may wear the electronic device during motion.

In some implementations, a signal acquisition apparatus configured to acquire a pulse wave signal is arranged in the electronic device, and the acquired pulse wave signal includes motion noise or is referred to as noise including a motion artifact. In an embodiment of the present disclosure, the signal acquisition apparatus may be a Photo Plethysmo Graphy (PPG) sensor and may acquire a PPG signal including motion noise. The PPG signal is, for example, d(n) shown in FIG. 2, where n may represent an $n^{th}$ processing cycle. Therefore, d(n) is a pulse wave signal that corresponds to the $n^{th}$ processing cycle and that includes motion noise.

In some implementations, a sensor configured to acquire motion signals that are of the electronic device and that correspond to the multi-dimensional directions may be arranged in the electronic device. In an embodiment of the present disclosure, the sensor may be a triaxial accelerometer and acquires motion signals of the electronic device that respectively correspond to an X axis direction, a Y axis direction, and a Z axis direction. The motion signals are, for example, x(n), y(n), and z(n) that correspond to the n th processing cycle shown in FIG. 2.

Therefore, the multi-dimensional directions in this embodiment may be the X axis direction, the Y axis direction, and the Z axis direction.

After the first pulse wave signal including the motion noise and the motion signals in the multi-dimensional directions are obtained in step S110, the following step S120 may be performed.

Step S120: Perform independent filtering processing on the motion signal in each dimensional direction, and determine a noise estimated value corresponding to each dimensional direction.

In this step, independent filtering processing is performed on the motion signal in each dimensional direction, to implement independent and parallel processing on multi-channel motion signals. Based on this, the noise estimated value corresponding each dimensional direction may be determined.

In an implementation, a plurality of filters may be designed. The plurality of filters are in a one-to-one correspondence with the multi-dimensional directions, and each filter independently performs filtering processing on a motion signal in a corresponding dimensional direction. In some implementations, the filter may be a Normalized Least Mean Square (NLMS) adaptive filter adopting an NLMS algorithm shown in FIG. 2.

In some implementations, each filter in the plurality of filters may perform filtering processing on a motion signal in a corresponding dimensional direction with reference to a filter coefficient thereof.

In this embodiment, the filter coefficient of each filter in the plurality of filters may be recorded as a filter coefficient corresponding to a corresponding dimensional direction.

Based on this, in an embodiment of the present disclosure, the performing independent filtering processing on the motion signal in each dimensional direction, and determining a noise estimated value corresponding to each dimensional direction in step S120 may include the following step S1201 and step S1202.

Step S1201: Determine, according to a motion signal in a first dimensional direction, a motion parameter corresponding to the first dimensional direction, where the first dimensional direction is any dimensional direction of the multi-dimensional directions.

In an embodiment of the present disclosure, the motion signal in the first dimensional direction includes: motion parameter values corresponding to the first dimensional direction at a series of sampling time points. At least some motion parameter values may be selected from the motion signal and are arranged according to a sequence of corresponding sampling time points, to obtain a motion parameter corresponding to the first dimensional direction. The motion parameter may be a vector.

In an implementation, the some selected motion parameter values may be motion parameter values respectively corresponding to a plurality of sampling time points relatively closest to a current time. For example, when a motion parameter is constructed, the motion parameter is constructed by using motion parameter values acquired within first is to 2*s*.

In this embodiment, it is assumed that the motion signals that are of the electronic device and that correspond to the X axis direction, the Y axis direction, and the Z axis direction are respectively x(n), Art), and z(n), motion parameters X(n), Y(n), and Z(n) respectively corresponding to the X axis direction, the Y axis direction, and the Z axis direction may be obtained.

Step S1202: Determine a noise estimated value corresponding to the first dimensional direction according to the motion parameter and a first filter coefficient corresponding to the first dimensional direction.

In the step, a noise estimated value in a corresponding dimensional direction is estimated with reference to the motion parameter and a filter coefficient of the filter. The noise estimated value may also be referred to as an adaptive estimated value of the first pulse wave signal d(n).

Figure 2:
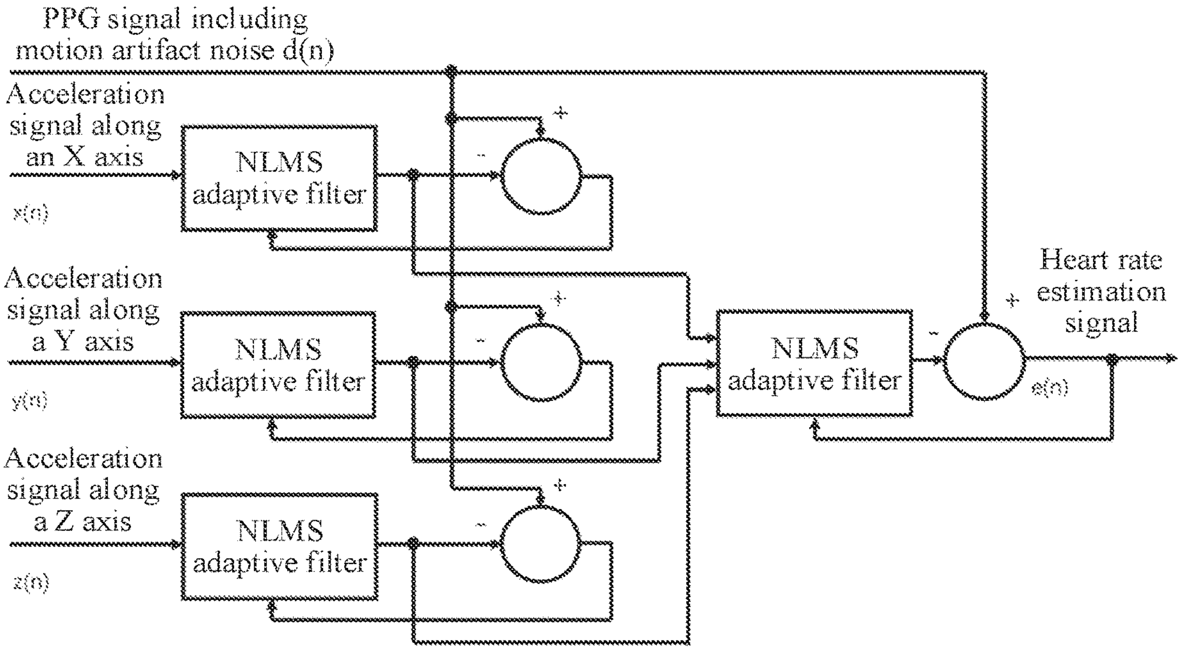
FIG. 2 is a block diagram of a signal flow according to an embodiment of the present disclosure.

Referring to FIG. 2, When there are three-dimensional directions, three independent and parallel NLMS adaptive filters may be designed correspondingly, and each NLMS adaptive filter independently estimates a noise estimated value corresponding to a corresponding dimensional direction.

In an implementation, the noise estimated value corresponding to each dimensional direction may be obtained through the following formula:

$d_x(n)=w_x(n)*X(n)$;

$d_y(n)=w_y(n)*Y(n)$; and $d_z(n)=w_z(n)*Z(n)$, where n represents the $n^{th}$ processing cycle, $d_x$, $d_y$, and $d_z$ respectively represent noise estimated values corresponding to the X axis direction, the Y axis direction, and the Z axis direction of the triaxial accelerometer, $w_x$, $w_y$, and $w_z$ respectively represent filter coefficients corresponding to the X axis direction, the Y axis direction, and the Z axis direction of the triaxial accelerometer, X(n), Y(n), and Z(n) respectively represent motion parameters corresponding to the X axis direction, the Y axis direction, and the Z axis direction of the triaxial accelerometer, and a * operation represents multiplication.

After the noise estimated value corresponding to each dimensional direction is determined in step S120, the following step S130 may be performed.

Step S130: Use the noise estimated values in the multi-dimensional directions as parallel input parameters, use the first pulse wave signal as an input parameter, and perform filtering processing on the first pulse wave signal, to obtain a second pulse wave signal.

In an implementation, another filter may be designed. The another filter has a fusion function and performs filtering processing on the first pulse wave signal with reference to the noise estimated value corresponding to each dimensional direction.

Referring to FIG. 2, the NLMS adaptive filter corresponding to each dimensional direction independently estimates a noise estimated value, the noise estimated value may be further inputted into an NLMS adaptive filter that has a fusion function, and the NLMS adaptive filter that has the fusion function may perform, with reference to each noise estimated value, filtering processing on the acquired first pulse wave signal that includes the motion noise, to obtain a second pulse wave signal, where the second pulse wave signal is a heart rate estimation signal e(n) shown in FIG. 2.

In some implementations, the filter that has the fusion function may perform filtering processing on the first pulse wave signal with reference to a filter coefficient of the filter and the noise estimated value corresponding to each dimensional direction.

in this embodiment, in the plurality of filters that are in a one-to-one correspondence with the multi-dimensional directions, the filter coefficient of each filter may be recorded as a filter coefficient corresponding to a corresponding dimensional direction. For the fusion filter, a filter coefficient of the fusion filter may be recorded as a filter coefficient corresponding to the multi-dimensional directions.

Based on this, in an embodiment of the present disclosure, the using the noise estimated values in the multi-dimensional directions as parallel input parameters, using the first pulse wave signal as an input parameter, and performing filtering processing on the first pulse wave signal, to obtain a second pulse wave signal in step S130 may include the following step S1301 and step S1302.

Step S1301: Use the noise estimated values in the multi-dimensional direction as the parallel input parameters, use the first pulse wave signal as the input parameter, and obtain a second filter coefficient corresponding to the multi-dimensional directions, where the second filter coefficient includes a first filter coefficient value corresponding to each dimensional direction.

In an implementation, the filter coefficient corresponding to the multi-dimensional directions may be obtained by using the following formula:

$A(n)=[a_x(n), a_y(n), a_z(n)]'$, where n represents the n th processing cycle, A represents the filter coefficient corresponding to the multi-dimensional directions, and $a_x$, $a_y$, and $a_z$ respectively represent filter coefficient values corresponding to the X axis direction, the Y axis direction, and the Z axis direction of the triaxial accelerometer. $a_x(n)$, $a_y(n)$, and $a_z(n)$ are all scalars, and A(n) is a vector constructed by using the three scalars.

Step S1302: Perform filtering processing on the first pulse wave signal according to the noise estimated value in each dimensional direction and the first filter coefficient value corresponding to each dimensional direction, to obtain the second pulse wave signal.

Based on the foregoing content, in an implementation, the second pulse wave signal may be obtained by using the following formula:

$$e(n)=d(n)-A(n)*P(n)=d(n)-[a_x(n)*d_x(n)+a_y(n)*d_y(n)+a_z(n)*d_z(n)];$$

$$A(n)=[a_x(n), a_y(n), a_z(n)]'; \text{ and}$$

$$P(n)=[d_x(n), d_y(n), d_z(n)]', \text{ where}$$

n represents the $n^{th}$ processing cycle, e represents the second pulse wave signal, d represents the first pulse wave signal that includes the motion noise, A represents the filter coefficient corresponding to the multi-dimensional directions, P(n) represents a vector constructed by using three scalars $d_x(n)$, $d_y(n)$, and $d_z(n)$, $d_x$, $d_y$, and $d_z$ respectively represent noise estimated values corresponding to the X axis direction, the Y axis direction, and the Z axis direction of the triaxial accelerometer, $a_x$, $a_y$, and $a_z$ respectively represent filter coefficient values corresponding to the X axis direction, the Y axis direction, and the Z axis direction of the triaxial accelerometer, and a * operation represents multiplication.

In this embodiment, when filtering processing is performed on the first pulse wave signal that includes the motion noise based on the noise estimated value corresponding to each dimensional direction, a physiological signal may be separated from a noise signal generated during movement of a user, to obtain a second pulse wave signal in which noise has been removed. The signal may accurately reflect a change of a heart rate of the user, so that the heart rate of the user obtained through estimation is closer to an actual heart rate of the user, thereby improving heart rate estimation accuracy.

As shown in FIG. 2, the second pulse wave signal is e(n). The signal may be further used for heart rate estimation.

It can be learned from the foregoing content that in this embodiment, independent and parallel processing is performed on the motion signal corresponding to each dimensional direction, to estimate a noise estimated value in a corresponding dimensional direction, and then fusion filtering processing is performed based on the noise estimated value in each dimensional direction, to reduce noise, so as to obtain the second pulse wave signal. A heart rate of the user is estimated by using the second pulse wave signal, and an adverse effect of motion noise on the heart rate estimation can be eliminated, thereby improving heart rate estimation accuracy.

In addition, in this embodiment of the present disclosure, in the parallel manner, independent adaptive filtering can be performed on the first pulse wave signal that includes the motion noise by using a motion signal of each channel of a multi-channel accelerometer, to independently estimate the first pulse wave signal to obtain a corresponding noise estimated value, and then an adaptive approximate result of each channel can be combined in the fusion filter with a lowest loss function of the first pulse wave signal, to improve the denoising effect. Therefore, when the fusion filter has motion artifact noise, a convergence response speed of denoising can be accelerated based on the parallel denoising manner, and a signal-to-noise ratio of a pulse wave heart rate signal is improved.

In addition to the parallel filter manner provided in this embodiment of the present disclosure, filtering noise reduction processing may be further performed according to a cascading sequence. For an implementation in which filtering is performed according to the cascading sequence, for example, an X axis motion signal, a Y axis motion signal, and a Z axis motion signal of the triaxial accelerometer are used as input signals for noise reduction, and adaptive filters are combined according to a cascading sequence of X axis→Y axis→Z and sequentially perform adaptive filtering, to perform filtering processing on a pulse wave signal that includes motion noise, to achieve a noise reduction effect.

However, in the implementation in which filtering is performed according to the cascading sequence, adaptive filters correspond to channels are set in a cascading manner. Therefore, in the cascaded adaptive filters, filtering input signals have a sequence. In some implementations, due to the sequence of the combined cascaded filters, a second-stage adaptive filter performs adaptive tracking according to a result outputted by a first-stage adaptive filter, and then a third-stage adaptive filter performs adaptive tracking according to a result outputted by the second-stage adaptive filter. Therefore, there is a sequence problem in an adaptive tracking sequence for calculation of a loss function, and an error signal of a latter-stage filter lags behind that of a previous-stage filter. Therefore, in a scenario in which a user wears a smartwatch and does a vigorous exercise such as running, the best effect cannot he necessarily achieved according to a specific cascading sequence (for example, X-Y-Z), and estimation and noise reduction on a heart rate signal by using an output signal are still inaccurate.

The parallel filtering solution provided in this embodiment of the present disclosure can resolve the problem. In some implementations, the filters corresponding to the channels are set in a parallel manner. Therefore, in the parallel filters, filtering input signals have no sequence. Based on this, the filter corresponding to each axis of the accelerometer may simultaneously perform independent filtering processing on an input signal, to obtain a corresponding noise estimated value. An additional filter is arranged, and the filter fuses signals by—using the noise estimated values as parallel input parameters, to perform filtering processing on the first pulse wave signal. During fusion, the fusion filter can further make a reasonable response according to a filtering status of each signal, to improve an input channel weight coefficient that can effectively reduce a loss function, thereby achieving an objective of multi-path parallel noise reduction.

in addition, in the implementation in which filtering is performed according to the cascading sequence, a reference signal of the second-stage adaptive filter uses an error signal e(n) of the first-stage adaptive filter as an input. Therefore, in terms of an amplitude of a signal, the reference signal of the second-stage adaptive filter is smaller than that of the first-stage adaptive filter. Similarly, a reference signal of the third-stage adaptive filter is smaller than that of the second-stage adaptive filter. That is, there is a stage-by-stage attenuation problem in the combined cascaded filters.

However, the parallel filtering solution provided in this embodiment of the present disclosure does not have the problem. This is because independent parallel computing is performed on the input signals in this embodiment of the present disclosure, there is no problem in which a reference signal of a filter is an error signal outputted by a previous-stage filter of the filter in the combined cascaded filters. Therefore, the convergence speed can be improved. In addition, the filters perform parallel output, so that an amplitude of an estimation signal outputted by each channel is uniform, but information about an error signal of a lower-stage filter is always lower than that of a higher-stage filter in the cascaded filters.

In this embodiment of the present disclosure, a parallel filtering solution is provided, and the solution is correspondingly described by using the foregoing content. Based on the foregoing content, it should be noted that, filtering processing on the first pulse wave signal may be a periodical processing process, Therefore, to improve a noise reduction effect, a filter coefficient of each filter may be periodically updated. Therefore, when filtering processing is performed in each filtering processing cycle, a corresponding noise estimated value is estimated according to a current latest filter coefficient of each filter. Therefore, the first filter coefficient may be a real-time updated filter coefficient.

Based on this, to describe a possible implementation in which a filter coefficient corresponding to each dimensional direction is updated, in an embodiment of the present disclosure, the first filter coefficient is a filter coefficient that corresponds to a first processing cycle and that corresponds to the first dimensional direction.

For example, the first processing cycle is an $n^{th}$ processing cycle (n is greater than or equal to 2). An X axis is used as an example, and the first filter coefficient corresponding to an X axis direction is $w_x(n)$.

Correspondingly, a filter coefficient that corresponds to the n th processing cycle and that corresponds to each dimensional direction may be obtained according to data corresponding to an $(n-1)^{th}$ processing cycle, to update the filter coefficient.

Based on this, before the determining a noise estimated value corresponding to the first dimensional direction according to the motion parameter and a first filter coefficient corresponding to the first dimensional direction in step S1202, the method further includes the following step A.

Step A: Obtain the first filter coefficient according to a target pulse wave signal that corresponds to a second processing cycle and that includes motion noise, a target motion parameter that corresponds to the second processing cycle and that corresponds to the first dimensional direction, and a third filter coefficient that corresponds to the second processing cycle and that corresponds to the first dimensional direction. The second processing cycle is a previous processing cycle adjacent to the first processing cycle.

in some implementations, the first processing cycle is a current processing cycle, and the second processing cycle is a previous processing cycle of the current processing cycle, For example, when the first processing cycle is the $n^{th}$ processing cycle, the second processing cycle is the $(n-1)^{th}$ processing cycle.

For example, the first processing cycle is the $n^{th}$ processing cycle. The target pulse wave signal may be d(n-1), the target motion parameter may be one of X(1-1), Y(n-1), and Z(n-1), X(n-1), Y(n-1), and Z(n-1) respectively correspond to the X axis direction, the Y axis direction, and the Z axis direction of the triaxial accelerometer, the third filter coefficient may be one of $w_x(n-1)$, $w_y(n-1)$, and $w_z(n-1)$, and $w_x(n-1)$, $w_y(n-1)$, and $w_z(n-1)$ respectively correspond to the X axis direction, the Y axis direction, and the Z axis direction of the triaxial accelerometer.

In this embodiment, for any dimensional direction, a filter coefficient that corresponds to a current processing cycle and that corresponds to the dimensional direction may be obtained according to a pulse wave signal that includes motion noise and that corresponds to a previous processing cycle, a motion parameter that corresponds to the previous processing cycle and that corresponds to the dimensional direction, and a filter coefficient that corresponds to the previous processing cycle and that corresponds to the dimensional direction. The process is repeated, and a fitter coefficient corresponding to any dimensional direction can be updated in real time.

The filter coefficient corresponding to each dimensional direction is updated in real time with reference to a real-time changed pulse wave signal that includes motion noise and a real-time changed motion signal in each dimensional direction and based on an existing filter coefficient corresponding to each dimensional direction. Therefore, when a noise estimated value is calculated based on the real-time updated filter coefficient corresponding to each dimensional direction, accurate estimation can be performed on the noise estimated value, and accurate filtering processing is supported, thereby achieving a good noise filtering effect.

Based on the foregoing content, in an embodiment of the present disclosure, the obtaining the first filter coefficient according to a target pulse wave signal that corresponds to a second processing cycle and that includes motion noise, a target motion parameter that corresponds to the second processing cycle and that corresponds to the first dimensional direction, and a third filter coefficient that corresponds to the second processing cycle and that corresponds to the first dimensional direction in step A may include the following step A1 to step A3.

Step A1: Obtain an error signal corresponding to the first dimensional direction according to the target pulse wave signal, the target motion parameter, and the third filter coefficient.

Based on the foregoing content, for example, the X axis direction, the Y axis direction, or the Z axis direction of the triaxial accelerometer is the first dimensional direction. A noise estimated value that corresponds to the $(n-1)^{th}$ processing cycle and that corresponds to the X axis direction is $d_x(n-1)$, a noise estimated value that corresponds to the $(n-1)^{th}$ processing cycle and that corresponds to the Y axis direction is $d_y(n-1)$, and a noise estimated value that corresponds to the $(n-1)^{th}$ processing cycle and that corresponds to the Z axis direction is $d_z(n-1)$.

In the step, the X axis is used as an example, and an error signal $e_x(n-1)$ corresponding to the X axis direction may be obtained according to the target pulse wave signal d(n-1), the target motion parameter X(n-1), and the noise estimated value $d_x(n-1)$ that corresponds to the $(n-1)^{th}$ processing cycle and that corresponds to the X axis direction.

Similarly, an error signal $e_y(n-1)$ corresponding to the Y axis direction may he obtained. and an error signal $e_z(n-1)$ corresponding to the Z axis direction may be obtained.

In an implementation, the error signal corresponding to each dimensional direction may be obtained through the following formula:

$e_x(n-1)=d(n-1)-w_x(n-1)*X(n-1)$;

$e_y(n-1)=d(n-1)-w_y(n-1)*Y(n-1)$; and $e_z(n-1)=d(n-1)-w_z(n-1)*Z(n-1)$, where n-1 represents the $(n-1)^{th}$ processing cycle, $e_x$, $e_y$, and $e_z$ respectively represent error signals corresponding to the X axis direction, the Y axis direction, and the Z axis direction of the triaxial accelerometer, d represents the first pulse wave signal that includes the motion noise, $w_x$, $w_y$, and $w_z$ respectively represent filter coefficients corresponding to the X axis direction, the Y axis direction, and the Z axis direction of the triaxial accelerometer, and X, Y, and Z respectively represent motion parameters corresponding to the X axis direction, the Y axis direction, and the Z axis direction of the triaxial accelerometer.

In another implementation, the X axis is used as an example, because $d_x(n)=w_x(n)*X(n)$, the error signal corresponding to each dimensional direction may be obtained through the following formula.

$e_x(n-1)-d_x(n-1)$;

$e_y(n-1)-d_y(n-1)$; and $e_z(n-1)-d_z(n-1)$, where n-1 represents the $(n-1)^{th}$ processing cycle, $e_x$, $e_y$, and $e_z$ respectively represent error signals corresponding to the X axis direction, the Y axis direction, and the Z axis direction of the triaxial accelerometer, d represents the first pulse wave signal that includes the motion noise, and $d_x$, $d_y$, and respectively represent noise estimated values corresponding to the X axis direction, the Y axis direction, and the Z axis direction of the triaxial accelerometer.

It should be noted that, referring to step S120, it can be learned that to obtain the second pulse wave signal corresponding to the $(n-1)^{th}$ processing cycle, the noise estimated value that corresponds to the $(n-1)^{th}$ processing cycle and that corresponds to each dimensional direction needs to be estimated in advance. Therefore, when the error signal corresponding to the $(n-1)^{th}$ processing cycle is calculated, the error signal may be directly calculated according to the estimated noise estimated value rather than according to the filter coefficient and the motion parameter:

Step A2: Obtain a filter adjustment coefficient according to the error signal and the target motion parameter.

In the step, the filter adjustment coefficient is obtained according to the error signal and the motion parameter, and a current filter coefficient is adjusted based on the adjustment coefficient, to obtain a new filter coefficient.

In an implementation, the filter adjustment coefficient corresponding to each dimensional direction may be obtained by using the following formula:

$\Delta w_x(n-1)=2*\mu*e_x(n-1)*(X(n-1)/(X(n-1)*X(n-1))+\varepsilon)$;

$\Delta w_y(n-1)=2*\mu*e_y(n-1)*(Y(n-1)/(Y(n-1)*Y(n-1))+\varepsilon)$; and $\Delta w_z(n-1)=2*\mu*e_z(n-1)*(Z(n-1)/(Z(n-1)*Z(n-1))+\varepsilon)$;

where n-1 represents the $(n-1)^{th}$ processing cycle, $\Delta w_x$, $\Delta w_y$, and $\Delta w_z$ respectively represent filter adjustment coefficients corresponding to the X axis direction, the Y axis direction, and the Z axis direction of the triaxial accelerometer, $e_x$, $e_y$, and $e_z$ respectively represent error signals corresponding to the X axis direction, the Y axis direction, and the Z axis direction of the triaxial accelerometer, X, Y, and Z respectively represent motion parameters corresponding to the X axis direction, the Y axis direction, and the Z axis direction of the triaxial accelerometer, and $\varepsilon$ is a constant.

Step A3: Obtain the first filter coefficient according to the filter adjustment coefficient and the third filter coefficient.

For example, the current processing cycle is the $n^{th}$ processing cycle, and the first filter coefficient is one of $w_x(n)$, $w_y(n)$, and $w_z(n)$. Correspondingly, the third filter coefficient is one of $w_x(n-1)$, $w_y(n-1)$, and $w_z(n-1)$.

Based on the foregoing content, in an implementation, the filter coefficient corresponding to each dimensional direction may be obtained by using the following formula:

$w_x(n)=w_x(n-1)+\Delta w_x(n-1)$;

$w_y(n)=w_y(n-1)+\Delta w_y(n-1)$; and $w_z(n)=w_z(n-1)+\Delta w_z(n-1)$, where n represents the $n^{th}$ processing cycle, n-1 represents the $(n-1)^{th}$ processing cycle, $w_x$, $w_y$, and $w_z$ respectively represent filter coefficients corresponding to the X axis direction, the Y axis direction, and the Z axis direction of the triaxial accelerometer, and $\Delta w_x$, $\Delta w_y$, and $\Delta w_z$ respectively represent filter adjustment coefficients corresponding to the X axis direction, the Y axis direction, and the Z axis direction of the triaxial accelerometer.

Therefore, in another embodiment of the present disclosure, after step A1, the filter coefficient corresponding to each dimensional direction may alternatively be directly calculated according to the following formula:

$\Delta w_x(n-1)=2*\mu*e_x(n-1)*(X(n-1)/(X(n-1)*X(n-1))+\varepsilon)$;

$\Delta w_y(n-1)=2*\mu*e_y(n-1)*(Y(n-1)/(Y(n-1)*Y(n-1))+\varepsilon)$; and $\Delta w_z(n-1)=2*\mu*e_z(n-1)*(Z(n-1)/(Z(n-1)*Z(n-1))+\varepsilon)$.

It can be learned from the foregoing content that in this embodiment of the present disclosure, the filter coefficient corresponding to each dimensional direction may be periodically updated, so that when filtering processing is periodically performed, the used filter coefficient corresponding to each dimensional direction is a real-time updated filter coefficient. Therefore, a noise reduction effect can be improved when filtering processing is performed based on the filter coefficient.

Based on a similar implementation principle, the filter coefficient of the fusion filter may also be periodically updated. Therefore, when filtering processing is performed on the first pulse wave signal that includes the motion noise, the real-time updated filter coefficient corresponding to the multi-dimensional directions may be used, so that the noise reduction effect is also improved when filtering processing is performed based on the filter coefficient.

Based on this, in an embodiment of the present disclosure, the second filter coefficient is a filter coefficient that corresponds to a first processing cycle and that corresponds to the multi-dimensional directions.

For example, the first processing cycle is the $n^{th}$ processing cycle (n is greater than or equal to 2), An X axis is used as an example, and the filter coefficient that corresponds to the $n^{th}$ processing cycle and that corresponds to the multi-dimensional directions is P(n).

Correspondingly, a filter coefficient of the fusion filter that corresponds to the $n^{th}$ processing cycle may be obtained according to data corresponding to the $(n-1)^{th}$ processing cycle, to update the filter coefficient corresponding to the multi-dimensional directions.

Based on this, the obtaining a second filter coefficient corresponding to the multi-dimensional directions in step S1301 includes: obtaining the second filter coefficient according to a pulse wave signal that corresponds to a second processing cycle and that is obtained through filtering processing, a fourth filter coefficient that corresponds to the second processing cycle and that corresponds to the multi-dimensional directions, and a noise estimated value that corresponds to the second processing cycle and that corresponds to each dimensional direction. The fourth filter coefficient includes a second filter coefficient value corresponding to each dimensional direction. The second processing cycle is a previous processing cycle adjacent to the first processing cycle.

In some implementations, the first processing cycle is a current processing cycle, and the second processing cycle is a previous processing cycle of the current processing cycle. For example, when the first processing cycle is the nt h processing cycle, the second processing cycle is the $(n-1)^{th}$ processing cycle.

in this embodiment, the filter coefficient corresponding to the multi-dimensional directions is updated according to a pulse wave signal e(n-1) that is obtained through filtering processing and that corresponds to the $(n-1)^{th}$ processing cycle, a filter coefficient A(n-1) that corresponds to the $(n-1)^{th}$ processing cycle and that corresponds to the multi-dimensional directions, and a noise estimated value $d_x(n-1)$, $d_y(n-1)$, and $d_z(n-1)$ that corresponds to the $(n-1)^{th}$ processing cycle and that corresponds to each dimensional direction, to obtain the filter coefficient that corresponds to the $n^{th}$ processing cycle and that corresponds to the multi-dimensional directions.

in this embodiment, the filter coefficient that corresponds to the current processing cycle and that corresponds to the multi-dimensional directions may be obtained according to the pulse wave signal that is obtained through filtering processing and that corresponds to the previous processing cycle, the filter coefficient that corresponds to the previous processing cycle and that corresponds to the multi-dimensional directions, and the noise estimated value that corresponds to the previous processing cycle and that corresponds to each dimensional direction. The process is repeated, and the filter coefficient corresponding to multi-dimensional directions can be updated in real time.

The filter coefficient is updated in real time with reference to the real-time changed pulse wave signal that is obtained through filtering processing and the real-time changed noise estimated values that corresponds to the dimensional directions and based on the existing filter coefficient that corresponds to the multi-dimensional directions. Therefore, when the second pulse wave signal is calculated based on the real-time updated filter coefficient that corresponds to the multi-dimensional directions, the second pulse wave signal can be accurately obtained, to achieve a better noise filtering effect.

In an implementation, the filter coefficient corresponding to the multi-dimensional directions may be obtained by using the following formula:

$A(n)=A(n-1)+2*\mu*e(n-1)*(P(n-1)/(P(n-1)*P(n-1))+\varepsilon)$;

$A(n-1)=[a_x(n-1), a_y(n-1), a_z(n-1)]'$; and $P(n-1)=[d_x(n-1), d_y(n-1), d_z(n-1)]'$, where n represents the $n^{th}$ processing cycle, n-1 represents the $(n-1)^{th}$ processing cycle, A represents the filter coefficient that corresponds to the multi-dimensional directions, μ is a step, e represents the second pulse wave signal, P(n-1) represents a vector constructed by using three scalars $d_x(n-1)$, $d_y(n-1)$, and $d_z(n-1)$, $d_x$, $d_y$, and $d_z$ respectively represent noise estimated values corresponding to the X axis direction, the Y axis direction, and the Z axis direction of the triaxial accelerometer. $a_x$, $a_y$, and $a_z$ respectively represent filter coefficient values corresponding to the X axis direction, the Y axis direction, and the Z axis direction of the triaxial accelerometer, a * operation represents multiplication, and ε is a constant.

It can be learned from the foregoing content that in this embodiment of the present disclosure, the filter coefficient of the fusion filter may be periodically updated, so that when filtering processing is periodically performed, the used filter coefficient is a real-time updated filter coefficient that corresponds to the multi-dimensional directions. Therefore, a noise reduction effect can be improved when filtering processing is performed based on the filter coefficient.

it should be noted that, the signal processing method provided in the embodiments of this application may be performed by a signal processing apparatus or a control module configured to perform the signal processing method in the signal processing apparatus. In this embodiment of this application, the signal processing apparatus provided in this embodiment of this application is described by using an example in which the signal processing apparatus executes the signal processing method.

Figure 3:
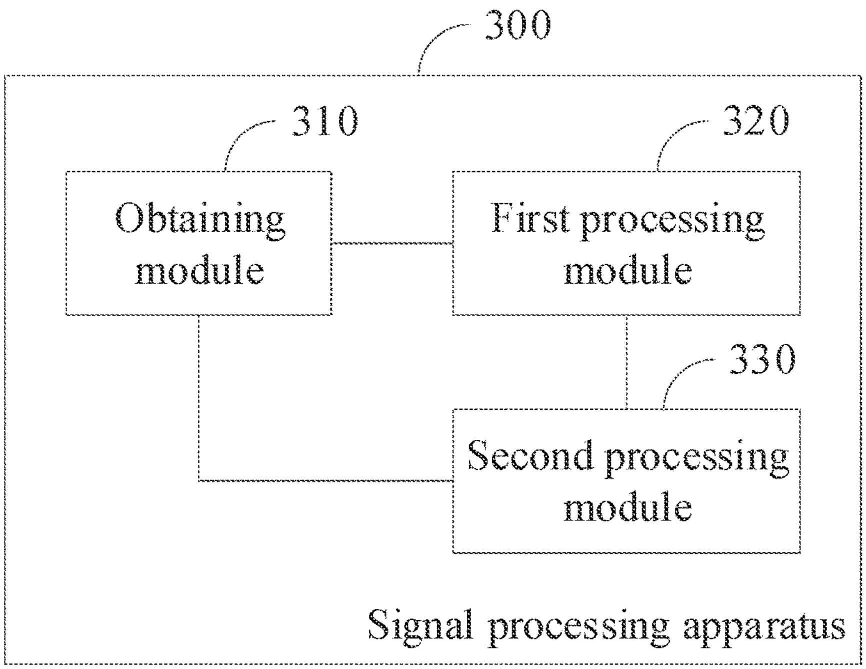
FIG. 3 is a block principle diagram of a signal processing apparatus according to an embodiment of the present disclosure.

As shown in FIG. 3, a signal processing apparatus 300 provided in this embodiment may include: an obtaining module 310, a first processing module 320. and a second processing module 330.

The obtaining module 310 is configured to obtain a first pulse wave signal and motion signals in multi-dimensional directions, where the first pulse wave signal includes motion noise. The first processing module 320 is configured to perform independent filtering processing on the motion signal in each dimensional direction, and determine a noise estimated value corresponding to each dimensional direction. The second processing module 330 is configured to use the noise estimated values in the multi-dimensional directions as parallel input parameters, use the first pulse wave signal as an input parameter, and perform—filtering processing on the first pulse wave signal, to obtain a second pulse wave signal. [01.02] In this embodiment, independent parallel processing is performed on the motion signal corresponding to each dimensional direction, to estimate a noise estimated value in a corresponding dimensional direction, and then fusion filtering processing is performed based on the noise estimated value in each dimensional direction, to reduce noise, so as to obtain the second pulse wave signal.

A heart rate of the user is estimated by using the second pulse wave signal, and an adverse effect of motion noise on the heart rate estimation can be eliminated, thereby improving heart rate estimation accuracy.

In an embodiment of the present disclosure, the first processing module 320 is configured to determine, according to a motion signal in a first dimensional direction, a motion parameter corresponding to the first dimensional direction, where the first dimensional direction is any dimensional direction of the multi-dimensional directions; and determine a noise estimated value corresponding to the first dimensional direction according to the motion parameter and a first filter coefficient corresponding to the first dimensional direction.

In an embodiment of the present disclosure, the first filter coefficient is a filter coefficient that corresponds to a first processing cycle and that corresponds to the first dimensional direction. The first processing module 320 is configured to: before the determining a noise estimated value corresponding to the first dimensional direction according to the motion parameter and a first filter coefficient corresponding to the first dimensional direction, obtain the first filter coefficient according to a target pulse wave signal that corresponds to a second processing cycle and that includes motion noise, a target motion parameter that corresponds to the second processing cycle and that corresponds to the first dimensional direction, and a third filter coefficient that corresponds to the second processing cycle and that corresponds to the first dimensional direction. The second processing cycle is a previous processing cycle adjacent to the first processing cycle.

In an embodiment of the present disclosure, the first processing module 320 is configured to obtain an error signal corresponding to the first dimensional direction according to the target pulse wave signal, the target motion parameter, and the third filter coefficient; obtain a filter adjustment coefficient according to the error signal and the target motion parameter; and obtain the first filter coefficient according to the filter adjustment coefficient and the third filter coefficient.

In an embodiment of the present disclosure, the second processing module 330 is configured to use the noise estimated values in the multi-dimensional direction as the parallel input parameters, use the first pulse wave signal as the input parameter, and obtain a second filter coefficient corresponding to the multi-dimensional directions, where the second filter coefficient includes a first filter coefficient value corresponding to each dimensional direction; and perform filtering processing on the first pulse wave signal according to the noise estimated value in each dimensional direction and the first filter coefficient value corresponding to each dimensional direction, to obtain the second pulse wave signal.

In an embodiment of the present disclosure, the second filter coefficient is a filter coefficient that corresponds to a first processing cycle and that corresponds to the multi-dimensional directions. The second processing module 330 is configured to obtain the second filter coefficient according to a pulse wave signal that corresponds to a second processing cycle and that is obtained through filtering processing, a fourth filter coefficient that corresponds to the second processing cycle and that corresponds to the multi-dimensional directions, and a noise estimated value that corresponds to the second processing cycle and that corresponds to each dimensional direction. The fourth filter coefficient includes a second filter coefficient value corresponding to each dimensional direction. The second processing cycle is a previous processing cycle adjacent to the first processing cycle.

In an embodiment of the present disclosure, the first processing module 320 may include a plurality of first filters. The plurality of first filters are m a one-to-one correspondence with the multi-dimensional directions, and each first filter is configured to perform independent filtering processing on a motion signal in a corresponding dimensional direction and determine a noise estimated value corresponding to the corresponding dimensional direction.

In an embodiment of the present disclosure, the second processing module 330 may include a second filter. The second filter is configured to use the noise estimated values in the multi-dimensional directions as parallel input parameters, use the first pulse wave signal as an input parameter, and perfbrm filtering processing on the first pulse wave signal, to obtain a second pulse wave signal.

The signal processing apparatus in this embodiment of this application may be an apparatus, or may be a component, an integrated circuit, or a chip in a terminal. The apparatus may be a mobile electronic device or may be a non-mobile electronic device. For example, the mobile electronic device may be a mobile phone, a tablet computer, a notebook computer, a palmtop computer, an in-vehicle electronic device, a wearable equipment, an—Ultra-Mobile Personal Computer (UMPC), a netbook, a Personal Digital Assistant (PDA), or the like. The non-mobile electronic device may be a server, a Network Atmched Storage (NAS), a personal computer, a television, a teller machine, a self-service machine, or the like. This is not specifically limited in this embodiment of this application.

The signal processing apparatus in this embodiment of this application may be an apparatus with an operating system. The operating system may be an Android operating system, am iOS operating system, or another possible operating system. This is not specifically limited in this embodiment of this application.

The signal processing apparatus provided in this embodiment of this application can implement the processes implemented in the method embodiment of FIG. 1. To avoid repetition, details are not described herein again.

Figure 4:
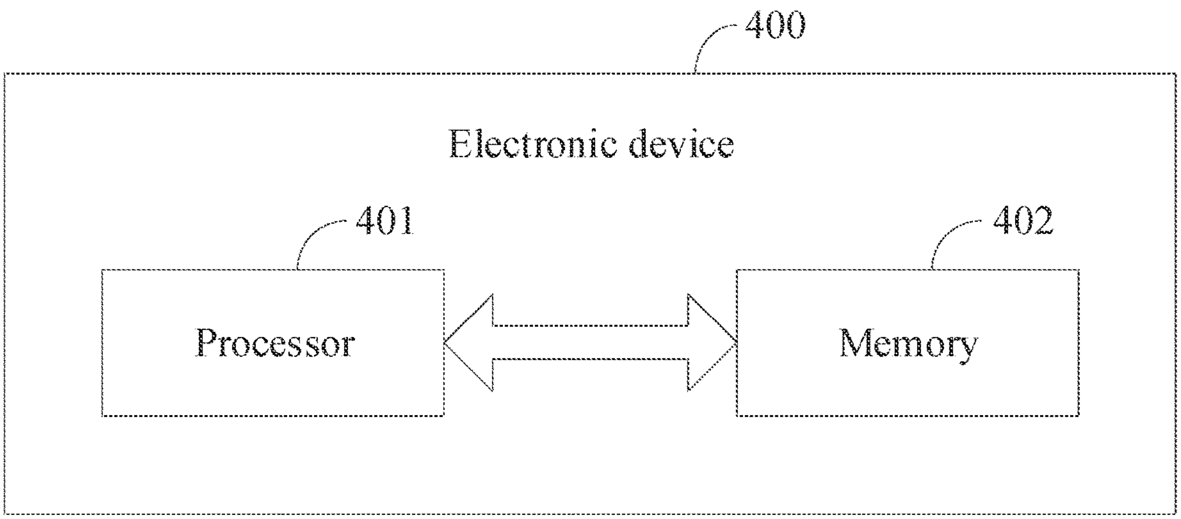
FIG. 4 is a block diagram of an electronic device according to an embodiment of the present disclosure.

In some implementations, as shown in FIG. 4, an embodiment of this application further provides an electronic device 400, including a processor 401, a memory 402, and a program or an instruction stored on the memory 402 and runnable on the processor 40I. For example, the program or the instruction is executed by the processor 401 to implement each process of the foregoing embodiments of the signal processing method, and the same technical effects can be achieved. To avoid repetition, details are not described herein again.

The memory 402 may be configured to store a software program and various data. The memory 402 may mainly include a first storage area that includes the program or the instruction and a second storage area that includes data. The first storage area may store an operating system, an application program or instruction required by at least one function (for example, a sound playback function and an image display function), and the like, In addition, the memory 402 may include a volatile memory or a non-volatile memory, or the memory 102 may include both a volatile memory and a non-volatile memory. The non-volatile memory may be a Read-Only Memory (ROM), a Programmable ROM (PROM), an Erasable PROM (EPROM), an Electrically EPROM (EEPROM), or a flash memory. The volatile memory may be a Random Access Memory (RAM), a Static RAM (SRAM), a Dynamic RAM (DRAM), a Synchronous DRAM (SDRAM), a Double Data Rate SDRAM (DDRSDRAM), an Enhanced SDRAM (ESDRAM), a Synch link DRAM (SLDRAM), and a Direct Rambus RAM (DRRAM). The memory 402 in this embodiment of this application includes but not limited to these memories and any other suitable types of memories.

The processor 401 may include one or more processing units. In some implementations, the processor 401 may integrate an application processor and a modem. The application processor mainly processes an operation involved in an operating system, a user interface, an application program, and the like. The modem mainly processes a wireless communication signal, for example, a baseband processor. It may be understood that the foregoing modem may either not be integrated into the processor 401.

It should be noted that, the electronic device in this embodiment of this application includes the mobile electronic device and the non-mobile electronic device.

Figure 5:
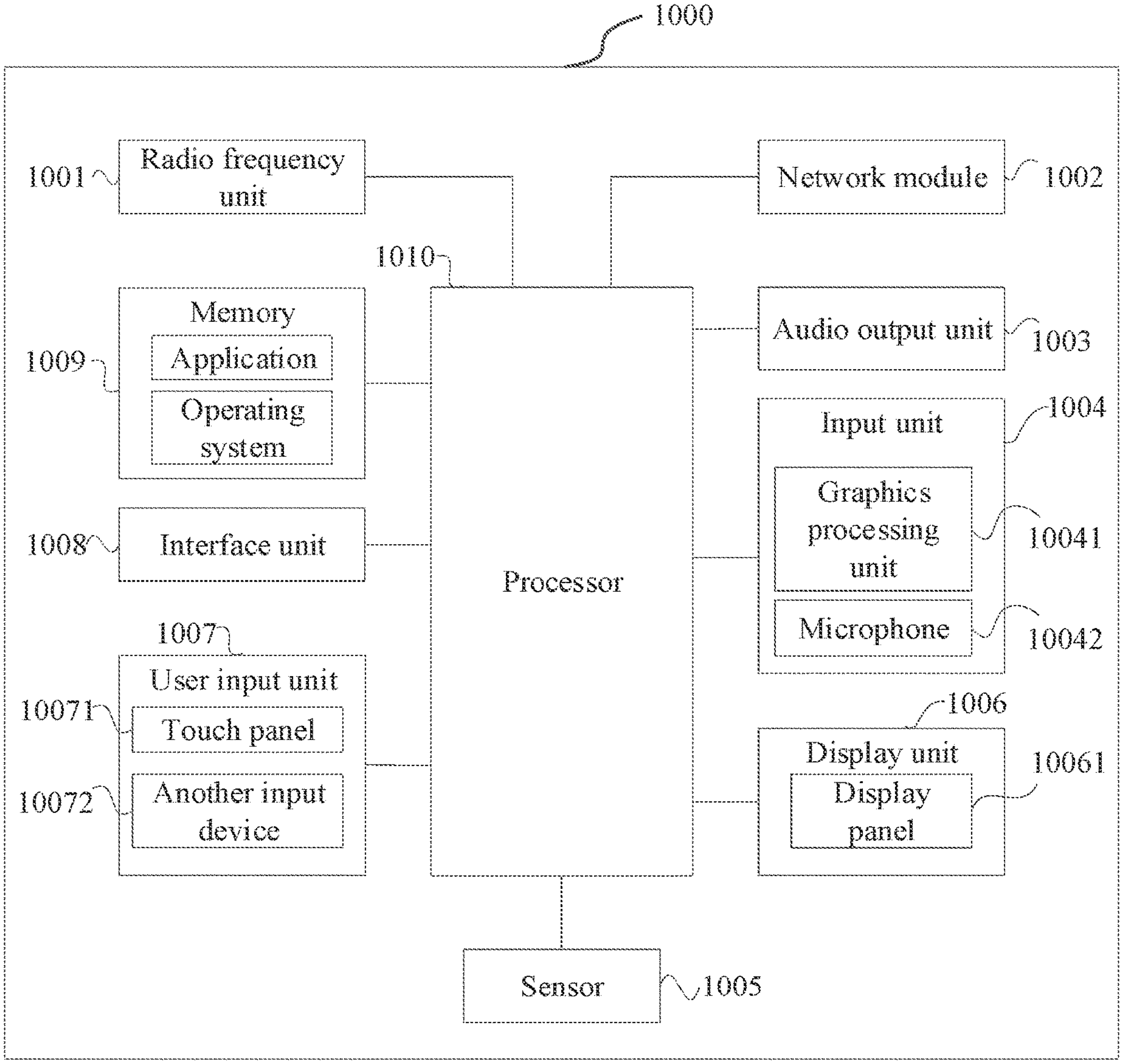
FIG. 5 is a block diagram of another electronic device according to an embodiment of the present disclosure.

FIG. 5 is a schematic diagram of a hardware structure of an electronic device 1000 according to an embodiment of this application.

The electronic device 1000 includes, but is not limited to, components such as a radio frequency unit 1001, a network module 1002, an audio output unit 1003, an input unit 1004, a sensor 1005, a display unit 1006, a user input unit 1007, an interface unit 1008, a memory 1009, and a processor 1010.

A person skilled in the art may understand that the electronic device 1000 may further include the power supply (such as a battery) for supplying power to the components. The power supply may logically connect to the processor 1010 by using a power supply management system, thereby implementing functions, such as charging, discharging, and power consumption management, by using the power supply management system. The electronic device structure shown in FIG. 5 constitutes no limitation on an external device, and the electronic device may include more or fewer components than those shown in the figure, or some components may be combined, or a different component deployment may be used, Details are described herein again.

The processor 1010 is configured to obtain a first pulse wave signal and motion signals in multi-dimensional directions, where the first pulse wave signal includes motion noise; perform independent filtering processing on the motion signal in each dimensional direction, and determine a noise estimated value corresponding to each dimensional direction; and use the noise estimated values in the multi-dimensional directions as parallel input parameters, use the first pulse wave signal as an input parameter, and perform filtering processing on the first pulse wave signal, to obtain a second pulse wave signal.

In this embodiment, independent parallel processing is performed on the motion signal corresponding to each dimensional direction, to estimate a noise estimated value in a corresponding dimensional direction, and then fusion filtering processing is performed based on the noise estimated value in each dimensional direction, to reduce noise, so as to obtain the second pulse wave signal. A heart rate of the user is estimated by using, the second pulse wave signal, and an adverse effect of motion noise on the heart rate estimation can be eliminated, thereby improving heart rate estimation accuracy.

in some implementations, the processor 1010 is configured to determine, according to a motion signal in a first dimensional direction, a motion parameter corresponding to the first dimensional direction, where the first dimensional direction is any dimensional direction of the multi-dimensional directions; and determine a noise estimated value corresponding to the first dimensional direction according to the motion parameter and a first filter coefficient corresponding to the first dimensional direction.

in some implementations, the first filter coefficient is a filter coefficient that corresponds to a first processing cycle and that corresponds to the first dimensional direction. The processor 1010 is configured to: before the determining a noise estimated value corresponding to the first dimensional direction according to the motion parameter and a first filter coefficient corresponding to the first dimensional direction, obtain the first filter coefficient according to a target pulse wave signal that corresponds to a second processing cycle and that includes motion noise, a target motion parameter that corresponds to the second processing—cycle and that corresponds to the first dimensional direction, and a third filter coefficient that corresponds to the second processing cycle and that corresponds to the first dimensional direction. The second processing cycle is a previous processing cycle adjacent to the first processing cycle.

In some implementations, the processor 1010 is configured to obtain an error signal corresponding to the first dimensional direction according to the target pulse wave signal, the target motion parameter, and the third filter coefficient; obtain a filter adjustment coefficient according to the error signal and the target motion parameter; and obtain the first filter coefficient according to the filter adjustment coefficient and the third filter coefficient.

In some implementations, the processor 1010 is configured to use the noise estimated values in the multi-dimensional direction as the parallel input parameters, use the first pulse wave signal as the input parameter, and obtain a second filter coefficient corresponding to the multi-dimensional directions, where the second filter coefficient includes a first filter coefficient value corresponding to each dimensional direction; and perform filtering processing on the first pulse wave signal according to the noise estimated value in each dimensional direction and the first filter coefficient value corresponding to each dimensional direction, to obtain the second pulse wave signal.

In some implementations, the second filter coefficient is a filter coefficient that corresponds to a first processing cycle and that corresponds to the multi-dimensional directions. The processor 1010 is configured to obtain the second filter coefficient according to a pulse wave signal that corresponds to a second processing cycle and that is obtained through filtering processing, a fourth filter coefficient that corresponds to the second processing cycle and that corresponds to the multi-dimensional directions, and a noise estimated value that corresponds to the second processing cycle and that corresponds to each dimensional direction. The fourth filter coefficient includes a second filter coefficient value corresponding to each dimensional direction. The second processing cycle is a previous processing cycle adjacent to the first processing cycle.

It should be understood that in this embodiment of this application, the input unit 1004 may include a Graphics Processing Unit (GPU) 10041 and a microphone 10042. The graphics processing unit 10041 performs processing on image data of a static picture or a video that is obtained by an image acquisition device (for example, a camera) in a video acquisition mode or an image acquisition mode. The display unit 1006 may include a display panel 10061, for example, the display panel 10061 configured in a form such as a liquid crystal display or an organic light-emitting diode. The user input unit 1007 includes a touch panel 10071 and another input device 10072. The touch panel 10071 is also referred to as a touchscreen. The touch panel 10071 may include two parts: a touch detection apparatus and a touch controller. The another input device 10072 may include, but not limited to, a physical keyboard, a functional key (such as a volume control key or a switch key), a track ball, a mouse, and a joystick, which are not described herein in detail. The memory 1009 may be configured to store a software program and various data, which includes, but not limited to, an application and an operating system. The processor 1010 may integrate an application processor and a modem processor. The application processor mainly processes an operating system, a user interface, an application program, and the like. The modem processor mainly processes wireless communication. It may be understood that the foregoing modem may either not be integrated into the processor 1010.

An embodiment of this application further provides a readable storage medium, storing a program or an instruction, where the program or the instruction is executed by a processor to implement each process of the foregoing embodiments of the signal processing method, and the same technical effect can be achieved. To avoid repetition, details are not repeated herein.

The processor is the processor in the electronic device in the foregoing embodiment. The readable storage medium includes a computer-readable storage medium such as a computer ROM, a RAM, a magnetic disk, or an optical disc.

An embodiment of this application further provides a chip, including a processor and a communication interface, where the communication interface is coupled to the processor, and the processor is configured to run a program or an instruction, to implement each process of the foregoing embodiments of the signal processing method, and the same technical effect can be achieved. To avoid repetition, details are not repeated herein.

It should be understood that, the chip mentioned in this embodiment of this application may also be referred to as a system-level chip, a system chip, a chip system, a system on chip, or the like.

It should be noted that, the terms "include," "including," or any other variation thereof in this specification is intended to cover a non-exclusive inclusion, which specifies the presence of stated processes, methods, objects, or apparatuses, but do not preclude the presence or addition of one or more other processes, methods, objects, or apparatuses. Without more limitations, elements defined by the sentence "including one" does not exclude that there are still other same elements in the processes, methods, objects, or apparatuses. In addition, it should be noted that, the scope of the methods and apparatuses in the implementations of this application is not limited to performing the functions in the order shown or discussed, but may further include performing the functions in a substantially simultaneous manner or in a reverse order depending on the functions involved. For example, the described methods may be performed in an order different from that described, and various steps may be added, omitted, or combined. In addition, features described with reference to some examples may be combined in other examples.

Through the descriptions of the foregoing implementations, a person skilled in the art may understand that the methods in the foregoing embodiments may be implemented by means of software and a necessary general hardware platform, and certainly, may also be implemented by hardware. Based on such an understanding, the technical solutions of this application essentially or the part contributing to the related art may be implemented in the form of a computer software product. The computer software product is stored in a storage medium (such as a ROM/RAM, a magnetic disk, or an optical disc), and includes several instructions for instructing a terminal (which may be a mobile phone, a computer, a server, a network device, or the like) to perform the method described in the embodiments of this application.

The embodiments of this application are described above with reference to the accompanying drawings. However, this application is not limited to the foregoing specific implementations. The foregoing specific implementations are illustrative instead of limitative. Enlightened by this application, a person of ordinary skill in the art can make many forms without departing from the idea of this application and the scope of protection of the claims. All of the forms fall within the protection of this application.

What is claimed is:

1. A signal processing method, comprising:

obtaining a first pulse wave signal and motion signals in multi-dimensional directions, wherein the first pulse wave signal comprises motion noise;

determining noise estimated values in the multi-dimensional directions, respectively, comprising:

performing independent filtering processing on a respective motion signal in each of the multi-dimensional directions, and determining a noise estimated value corresponding to each of the multi-dimensional directions, comprising:

determining, according to a motion signal in a first dimensional direction, a motion parameter corresponding to the first dimensional direction, wherein the first dimensional direction is one of the multi-dimensional directions; and determining a noise estimated value corresponding to the first dimensional direction according to the motion parameter and a first filter coefficient corresponding to the first dimensional direction; and using the noise estimated values in the multi-dimensional directions as parallel input parameters, using the first pulse wave signal as an input parameter, and performing digital filtering processing on the first pulse wave signal to obtain a second pulse wave signal in which the motion noise is removed; and estimating a heart rate of a user from the second pulse wave signal in which the motion noise is removed.

2. The method according to claim 1, wherein the first filter coefficient is a filter coefficient that corresponds to a first processing cycle and that corresponds to the first dimensional direction; and before the determining a noise estimated value corresponding to the first dimensional direction according to the motion parameter and a first filter coefficient corresponding to the first dimensional direction, the method further comprises:

obtaining the first filter coefficient according to:

a target pulse wave signal that corresponds to a second processing cycle and that comprises motion noise, a target motion parameter that corresponds to the second processing cycle and that corresponds to the first dimensional direction, and a third filter coefficient that corresponds to the second processing cycle and that corresponds to the first dimensional direction, wherein the second processing cycle is a previous processing cycle adjacent to the first processing cycle.

3. The method according to claim 2, wherein the obtaining the first filter coefficient according to a target pulse wave signal that corresponds to a second processing cycle and that comprises motion noise, a target motion parameter that corresponds to the second processing cycle and that corresponds to the first dimensional direction, and a third filter coefficient that corresponds to the second processing cycle and that corresponds to the first dimensional direction comprises:

obtaining an error signal corresponding to the first dimensional direction according to the target pulse wave signal, the target motion parameter, and the third filter coefficient;

obtaining a filter adjustment coefficient according to the error signal and the target motion parameter; and obtaining the first filter coefficient according to the filter adjustment coefficient and the third filter coefficient.

4. The method according to claim 1, wherein the using the noise estimated values in the multi-dimensional directions as parallel input parameters, using the first pulse wave signal as an input parameter, and performing digital filtering processing on the first pulse wave signal to obtain a second pulse wave signal in which the motion noise is removed comprises:

using the noise estimated values in the multi-dimensional direction as the parallel input parameters, using the first pulse wave signal as the input parameter, and obtaining a second filter coefficient corresponding to the multi-dimensional directions, wherein the second filter coefficient comprises a first filter coefficient value corresponding to each of the multi-dimensional directions; and performing filtering processing on the first pulse wave signal according to the noise estimated value in each of the multi-dimensional directions and the first filter coefficient value corresponding to each of the multi-dimensional directions, to obtain the second pulse wave signal.

5. The method according to claim 4, wherein the second filter coefficient is a filter coefficient that corresponds to a first processing cycle and that corresponds to the multi-dimensional directions, wherein the obtaining a second filter coefficient corresponding to the multi-dimensional directions comprises:

obtaining the second filter coefficient according to a pulse wave signal that corresponds to a second processing cycle and that is obtained through filtering processing, a fourth filter coefficient that corresponds to the second processing cycle and that corresponds to the multi-dimensional directions, and a noise estimated value that corresponds to the second processing cycle and that corresponds to each of the multi-dimensional directions, wherein the fourth filter coefficient comprises a second filter coefficient value corresponding to each of the multi-dimensional directions, and wherein the second processing cycle is a previous processing cycle adjacent to the first processing cycle.

6. An electronic device, comprising: a processor, a memory, and a program or an instruction stored in the memory and runnable on the processor, wherein the program or the instruction is configured to be executed by the processor to implement a signal processing method comprising:

obtaining a first pulse wave signal and motion signals in multi-dimensional directions, wherein the first pulse wave signal comprises motion noise;

determining noise estimated values in the multi-dimensional directions, respectively, comprising:

performing independent filtering processing on a respective motion signal in each of the multi-dimensional directions, and determining a noise estimated value corresponding to each of the multi-dimensional directions, comprising:

determining, according to a motion signal in a first dimensional direction, a motion parameter corresponding to the first dimensional direction, wherein the first dimensional direction is one of the multi-dimensional directions; and determining a noise estimated value corresponding to the first dimensional direction according to the motion parameter and a first filter coefficient corresponding to the first dimensional direction; and using the noise estimated values in the multi-dimensional directions as parallel input parameters, using the first pulse wave signal as an input parameter, and performing digital filtering processing on the first pulse wave signal to obtain a second pulse wave signal in which the motion noise is removed; and estimating a heart rate of a user from the second pulse wave signal in which the motion noise is removed.

7. The electronic device according to claim 6, wherein the first filter coefficient is a filter coefficient that corresponds to a first processing cycle and that corresponds to the first dimensional direction; and before the determining a noise estimated value corresponding to the first dimensional direction according to the motion parameter and a first filter coefficient corresponding to the first dimensional direction, the signal processing method further comprises:

obtaining the first filter coefficient according to:

a target pulse wave signal that corresponds to a second processing cycle and that comprises motion noise, a target motion parameter that corresponds to the second processing cycle and that corresponds to the first dimensional direction, and a third filter coefficient that corresponds to the second processing cycle and that corresponds to the first dimensional direction, wherein the second processing cycle is a previous processing cycle adjacent to the first processing cycle.

8. The electronic device according to claim 7, wherein the obtaining the first filter coefficient according to a target pulse wave signal that corresponds to a second processing cycle and that comprises motion noise, a target motion parameter that corresponds to the second processing cycle and that corresponds to the first dimensional direction, and a third filter coefficient that corresponds to the second processing cycle and that corresponds to the first dimensional direction comprises:

obtaining an error signal corresponding to the first dimensional direction according to the target pulse wave signal, the target motion parameter, and the third filter coefficient;

obtaining a filter adjustment coefficient according to the error signal and the target motion parameter; and obtaining the first filter coefficient according to the filter adjustment coefficient and the third filter coefficient.

9. The electronic device according to claim 6, wherein the using the noise estimated values in the multi-dimensional directions as parallel input parameters, using the first pulse wave signal as an input parameter, and performing digital filtering processing on the first pulse wave signal to obtain a second pulse wave signal in which the motion noise is removed comprises:

using the noise estimated values in the multi-dimensional direction as the parallel input parameters, using the first pulse wave signal as the input parameter, and obtaining a second filter coefficient corresponding to the multi-dimensional directions, wherein the second filter coefficient comprises a first filter coefficient value corresponding to each of the multi-dimensional directions; and performing filtering processing on the first pulse wave signal according to the noise estimated value in each of the multi-dimensional directions and the first filter coefficient value corresponding to each of the multi-dimensional directions, to obtain the second pulse wave signal.

10. The electronic device according to claim 9, wherein the second filter coefficient is a filter coefficient that corresponds to a first processing cycle and that corresponds to the multi-dimensional directions, wherein the obtaining a second filter coefficient corresponding to the multi-dimensional directions comprises:

obtaining the second filter coefficient according to a pulse wave signal that corresponds to a second processing cycle and that is obtained through filtering processing, a fourth filter coefficient that corresponds to the second processing cycle and that corresponds to the multi-dimensional directions, and a noise estimated value that corresponds to the second processing cycle and that corresponds to each of the multi-dimensional directions, wherein the fourth filter coefficient comprises a second filter coefficient value corresponding to each of the multi-dimensional directions, and wherein the second processing cycle is a previous processing cycle adjacent to the first processing cycle.

11. A non-transitory computer-readable medium storing a program or instruction, wherein the program or the instruction is configured to executed by a processor to implement a signal processing method comprising:

obtaining a first pulse wave signal and motion signals in multi-dimensional directions, wherein the first pulse wave signal comprises motion noise;

determining noise estimated values in the multi-dimensional directions, respectively, comprising:

performing independent filtering processing on a respective motion signal in each of the multi-dimensional directions, and determining a noise estimated value corresponding to each of the multi-dimensional directions, comprising:

determining, according to a motion signal in a first dimensional direction, a motion parameter corresponding to the first dimensional direction, wherein the first dimensional direction is one of the multi-dimensional directions; and determining a noise estimated value corresponding to the first dimensional direction according to the motion parameter and a first filter coefficient corresponding to the first dimensional direction; and using the noise estimated values in the multi-dimensional directions as parallel input parameters, using the first pulse wave signal as an input parameter, and performing digital filtering processing on the first pulse wave signal to obtain a second pulse wave signal in which the motion noise is removed; and estimating a heart rate of a user from the second pulse wave signal in which the motion noise is removed.

12. The non-transitory computer-readable medium according to claim 11, wherein the first filter coefficient is a filter coefficient that corresponds to a first processing cycle and that corresponds to the first dimensional direction; and before the determining a noise estimated value corresponding to the first dimensional direction according to the motion parameter and a first filter coefficient corresponding to the first dimensional direction, the signal processing method further comprises:

obtaining the first filter coefficient according to:

a target pulse wave signal that corresponds to a second processing cycle and that comprises motion noise, a target motion parameter that corresponds to the second processing cycle and that corresponds to the first dimensional direction, and a third filter coefficient that corresponds to the second processing cycle and that corresponds to the first dimensional direction, wherein the second processing cycle is a previous processing cycle adjacent to the first processing cycle.

13. The non-transitory computer-readable medium according to claim 12, wherein the obtaining the first filter coefficient according to a target pulse wave signal that corresponds to a second processing cycle and that comprises motion noise, a target motion parameter that corresponds to the second processing cycle and that corresponds to the first dimensional direction, and a third filter coefficient that corresponds to the second processing cycle and that corresponds to the first dimensional direction comprises:

obtaining an error signal corresponding to the first dimensional direction according to the target pulse wave signal, the target motion parameter, and the third filter coefficient;

obtaining a filter adjustment coefficient according to the error signal and the target motion parameter; and obtaining the first filter coefficient according to the filter adjustment coefficient and the third filter coefficient.

14. The non-transitory computer-readable medium according to claim 11, wherein the using the noise estimated values in the multi-dimensional directions as parallel input parameters, using the first pulse wave signal as an input parameter, and performing digital filtering processing on the first pulse wave signal to obtain a second pulse wave signal in which the motion noise is removed comprises:

using the noise estimated values in the multi-dimensional direction as the parallel input parameters, using the first pulse wave signal as the input parameter, and obtaining a second filter coefficient corresponding to the multi-dimensional directions, wherein the second filter coefficient comprises a first filter coefficient value corresponding to each of the multi-dimensional directions; and performing filtering processing on the first pulse wave signal according to the noise estimated value in each of the multi-dimensional directions and the first filter coefficient value corresponding to each of the multi-dimensional directions, to obtain the second pulse wave signal.

15. The non-transitory computer-readable medium according to claim 14, wherein the second filter coefficient is a filter coefficient that corresponds to a first processing cycle and that corresponds to the multi-dimensional directions, wherein the obtaining a second filter coefficient corresponding to the multi-dimensional directions comprises:

obtaining the second filter coefficient according to a pulse wave signal that corresponds to a second processing cycle and that is obtained through filtering processing, a fourth filter coefficient that corresponds to the second processing cycle and that corresponds to the multi-dimensional directions, and a noise estimated value that corresponds to the second processing cycle and that corresponds to each of the multi-dimensional directions, wherein the fourth filter coefficient comprises a second filter coefficient value corresponding to each of the multi-dimensional directions, and wherein the second processing cycle is a previous processing cycle adjacent to the first processing cycle.

* * * * *